United States Patent [19]

Picunko et al.

[11] 4,294,259

[45] Oct. 13, 1981

[54] METHOD AND APPARATUS FOR CHARACTERIZING BLOOD FLOW THROUGH THE HEART

[75] Inventors: Thomas Picunko, Bronxville, N.Y.; Henry H. Kramer, Mahwah, N.J.; Naim G. Dam, Bayside; Robert I. Gray, Irvington, both of N.Y.

[73] Assignee: Bios Inc., Valhalla, N.Y.

[21] Appl. No.: 854,537

[22] Filed: Nov. 25, 1977

[51] Int. Cl.³ .............................................. A61B 5/02
[52] U.S. Cl. ................................. 128/653; 250/363 S
[58] Field of Search ................ 340/324 AD; 250/273, 250/363 S; 346/33 ME; 364/413-417, 555; 128/2 A, 2.05 F, 2.05 V, 2.06 R, 653-654

[56] References Cited

U.S. PATENT DOCUMENTS

| | | | |
|---|---|---|---|
| 3,784,789 | 1/1974 | Broek | 364/416 |
| 3,995,259 | 11/1976 | Harris et al. | 340/324 AD |
| 4,101,961 | 7/1978 | Reiber | 128/653 |
| 4,111,191 | 9/1978 | Shaw | 128/2 A |

FOREIGN PATENT DOCUMENTS

| | | | |
|---|---|---|---|
| 848072 | 3/1977 | Belgium | 128/2 A |
| 1444651 | 5/1974 | United Kingdom | 128/2 A |

OTHER PUBLICATIONS

Ray, C. D., "Nuclear Medicine," in *Medical Engineering*, chapter 60, p. 739, Yrbk Publishers, Chic. 1974.

DeJong, L. P. et al., "Automatic Detection of Left Ventricular Outline in Angiographs Using Television Signal Processing Techniques," IEEE Transactions on Biomed Engr., vol. BME-22, No. 3, May 1975, pp. 230-237.

Covvey, H. D., "Measuring the Heart with a Realtime Computing System," *Data Processing Magazine*, May 1970.

Willson, K. et al., "Digital Processing of Ultrasound Cardiac Images," Conf. Proceedings of the 2nd European Congress on Ultrasonics in Medicine, Munich, Germany, 12-16 May 1975, pp. 103-107.

Hoffman, G. et al., *The Method of Radiocardiographic Function Analysis*, Nuclear Medizin, vol. 7, pp. 350-370, 1968.

Bacharach, S. L. et al., *An ECG-gated Scintillation Probe-Mini-Computer System for Real-Time Const. & Analysis of High Temporal Resolution LVV Curves*, JNM vol. 17, p. 557, 1976.

Albert, N. et al., *Noninvasive Nuclear Kinecardiography*, JNM, vol. 15, No. 12, Dec. 1974, pp. 1182-1184.

Sano, R. M. et al., *A Nuclear Cardiology Module*, SNM 24th Mtg., Instr. 2: Poster Session, Jun. 24, 1977.

Wagner, H. et al., *The Nuclear Stethoscope: A Simple Device for Generation of LVV Curves*, Amer. Jrnl. Cardiology, vol. 38, Nov. 23, 1976.

Bacharach, S. L. et al., *ECG-gated Scintillation Probe Measurement of LV Function*, Trans. of the Amer. Nucl. Soc., vol. 22:117, 1975.

Nickoloff, E. L., Thesis: *The Physics of LV Performance Measurements with Radioactive Tracers*, Sch. of Hyg. & Pub. Hlth., Johns Hopkins Univ., Jan. 1977.

Primary Examiner—Robert W. Michell
Assistant Examiner—Francis J. Jaworski
Attorney, Agent, or Firm—MCAulay, Fields, Fisher, Goldstein & Nissen

[57] ABSTRACT

An automated method and improved device provide a measurement of blood flow through the heart by the detection and analysis of radioactivity emitted by a radioactive tracer introduced into a patient's bloodstream. Real time, cardiac cycle by cardiac cycle information is processed and displayed to provide diagnostically useful information on an essentially ongoing basis as the patient is being tested.

18 Claims, 13 Drawing Figures

METHOD AND APPARATUS FOR CHARACTERIZING BLOOD FLOW THROUGH THE HEART

BACKGROUND OF THE INVENTION

This invention relates to diagnostic techniques of characterizing blood flow through the heart by detecting radioactivity from a radioactive blood pool tracer injected into the patient's bloodstream and displaying the resultant data. More specifically, it relates to the use of a moveable cursor display to locate data of interest and the use of a microcomputer to calculate certain indices of heart performance in the course of characterizing blood flow through the heart.

The characterization of blood flow through the heart using radioactive blood pool tracers injected into the patient's bloodstream is well known in the art. Illustrations of the application of this principle are found in Belgian Pat. No. 848072 and the article by Wagner, et. al., "The Nuclear Stethoscope: A Simple device for Generation of Left Ventricular Volume Curves", *The American Journal of Cardiology*, Volume 38, Nov. 23, 1976, pp. 747-750.

Other pertinent literature references include:

Hoffman, G., and N. Kleine: "The Method of Radiocardiographic Function Analysids:" ("DIe Methode der radiokardiographischen Funktionsanalyse"), *Nuclear-Medizin*, Vol. 7, pp. 350-370, 1968.

Bacharach, S. L., et. al., "Gated Scintillation Probe Measurement of Left Ventricular Function", *Transactions of the American Nuclear Society*, Vol. 22: 117, 1975.

Bacharach, S. L., et al., "An ECG-gated scintillation probe-minicomputer system for real-time construction and analysis of high temporal resolution left ventricular volume curves", *Journal of Nuclear Medicine*, Vol. 17: 557, 1976.

Nickloff, E. L., Thesis: "The Physics of Left Ventricular Performance Measurements with Radioactive Tracers", School of Hygiene and Public Health of the Johns Hopkins University, January 1977.

As illustrated in the Belgian patent and the Wagner article, blood flow through the heart may be characterized by injecting a radioactive blood pool tracer into the patient's bloodstream and detecting resulting changes in radioactivity from the heart as it contracts and expands. Typically, a radiation detector is located adjacent to the patient's chest wall in order to monitor radiation from the left ventricle of the heart. In order to synchronize the acquisition of data to the patient's heartbeat, the patient is connected an electrocardiogram apparatus. The patient's heartbeat interval is divided into a plurality of shorter temporal subintervals. The number of radiation counts associated with each subinterval is detected and stored. Radiation counts are detected during successive heartbeats and the counts are added to the counts previously detected during each of the corresponding subintervals. The resultant data are cumulatively stored in memory. The memory contents are repeatedly displayed on a CRT screen. This display is in the form of a bar graph in which the peaks vary in amplitude as a function of time proportional to the changing volume of the left ventircle. After the desired number of heartbeats have occurred, a photograph is taken of the CRT display.

Similarly, the radiation detector is relocated to a suitable position on the patient's chest wall in order to measure the radiation from local body tissues in the vicinity of the heart. This radiation is commonly referred to as background radiation. Radiation counts are detected and accumulated as in the case of radiation from the left ventricle of the heart. Again, after the desired number of heartbeats have occurred, a photograph is taken of the CRT display.

At this point manual measurements are taken of the photographic data in order to calculate useful performance indices of the heart function such as ejection fraction, etc.

It is apparent that the major disadvantage and limitation of the conventional blood flow characterization method is the need for manual measurements of photographic data. This technique is time-consuming, expensive and the quality of the output varies with the skills of the technician.

Accordingly, it is an object of the invention to provide an atuomated method of obtaining various performance indices of heart function.

It is a further object of the invention to provide a real-time method for locating the left ventricle of the heart and for locating a suitable position for measuring tissue background activity in proximity to the heart.

It is still a further object of the invention to provide improved apparatus for atuomatically obtaining various performance indices of heart function.

SUMMARY OF THE INVENTION

The foregoing and other objects and advantages which will be apparent in the following detailed description of the preferred embodiment, or in the practice of the invention, are achieved by the invention disclosed herein, which generally may be characterized as an atuomated method and improved apparatus for characterizing blood flow through the heart, the method including:

(a) introducing a radioactive blood pool tracer into a patient's bloodstream;

(b) deriving a synchronization signal from the patient's electrocardiogram;

(c) synchronizing the horizontal axis data of a cathode ray tube display to the patient's electrocardiogram;

(d) displaying the patient's cardiac cycle on the horizontal time axis divided into a predetermined number of temporal subintervals;

(e) positioning nuclear detection means in proximity to the patient's chest wall in the vicinity of the heart where the field of view of the nuclear detection means including any part of the heart is minimized for detecting counts representative of tissue background activity;

(f) storing the number of tissue background counts in a separate memory location;

(g) acquiring tissue background counts for a predetermined length of time;

(h) cumulatively adding and storing tissue background counts occurring during the predetermined length of acquisition time;

(i) displaying the contents of the memory location containing the accumulated tissue background counts;

(j) positioning nuclear detection means over the left ventricle region of the patient's chest for detecting counts representative of left ventricular activity;

(k) synchronizing the detection of left ventricle counts to the patient's electrocardiogram;

(l) storing the number of left ventricle counts in separate memory locations corresponding to each temporal subinterval occurring during the patient's cardiac cycle;

(m) acquiring left ventricle counts for a predetermined length of time;

(n) cumulatively adding and storing left ventricle counts occurring during corresponding subintervals of successive cardiac cycles;

(o) displaying the contents of the memory location containing the accumulated left ventricle counts;

(p) positioning an adjustable cursor system to locate data of interest; and (q) programming electronic signal processing means to access the stored accumulated tissue background counts and stored accumulated left ventricle counts upon which measurements are performed and displaying a diagnostic message indicating the value of a selected indicator of heart performance; and the improvement in the apparatus comprising:

(1) an adjustable cursor control system for locating data of interest on the cathode ray display;

(2) automatic means for accessing the stored data of interset and calculating selected indices of heart performance; and (3) automatic means for displaying diagnostic messages indicating the values of the selected indices of heart performance.

DETAILED DESCRIPTION OF PREFERRED EMBODIMENTS

Figure 2:
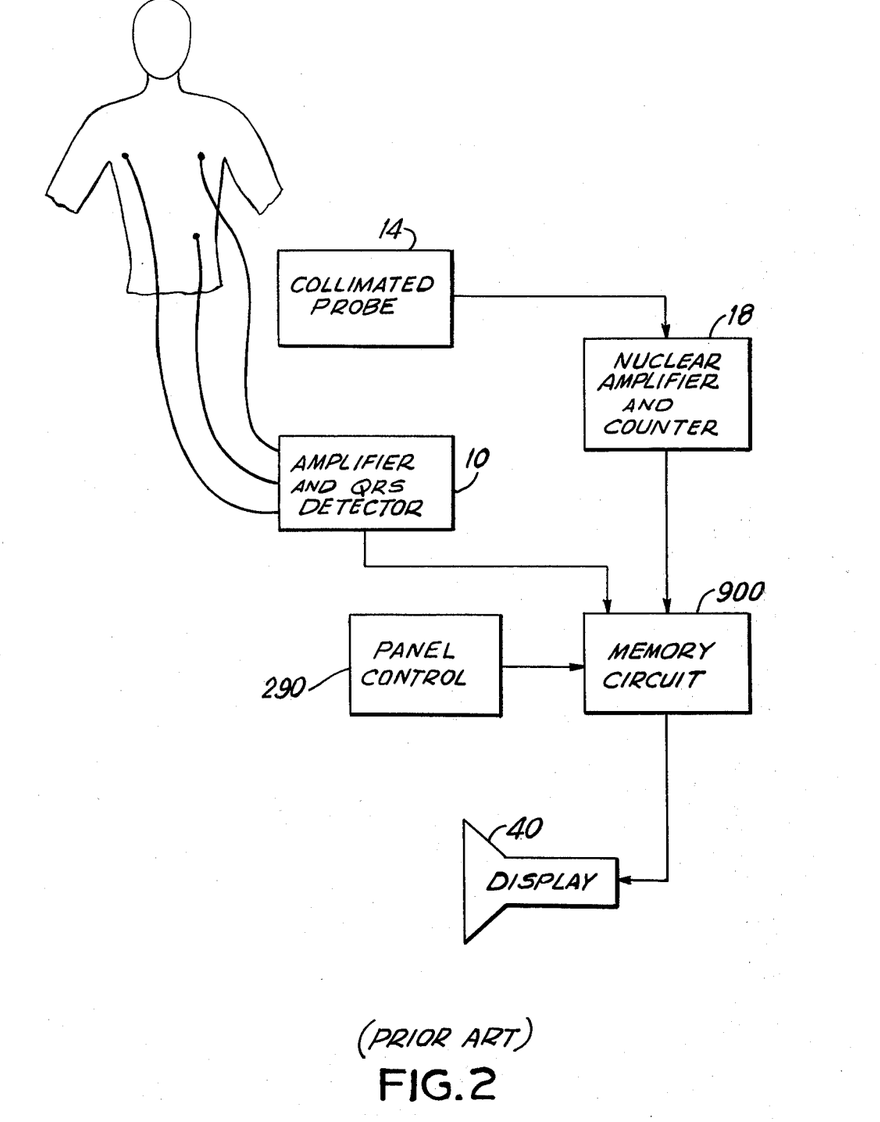
FIG. 2 is a simplified block diagram of the prior art apparatus for characterizing blood flow through the heart.

Referring to FIG. 2, a simplified block diagram of the prior art apparatus is illustrated. The apparatus generally consists of a collimated probe 14 consisting of a lead collimator, thallium-doped sodium iodide crystal and a photomultiplier detector, the output of which leads to nuclear amplifier and counter 18. This counter amplifies, selects and counts nuclear events of the desired energy level. The output of nuclear amplifier and counter 18 leads to memory circuit 900 which cumulatively stores counts in synchronism with the output of amplifier and QRS detector 10 and in conjunction with the settings of panel controls 290. The output of memory circuit 900 passes to display 40 where the contents of memory are caused to repetitively sweep across the display.

Figure 3A:
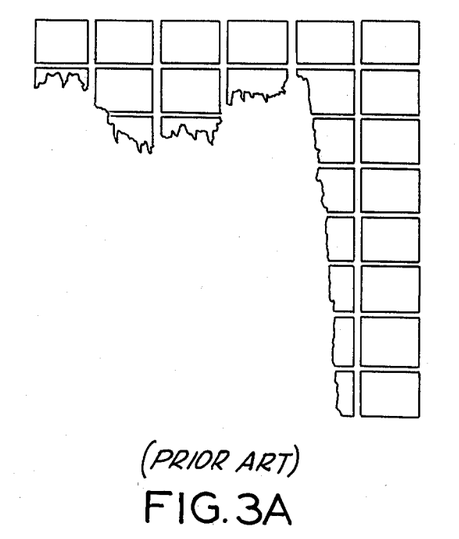
FIG. 3A is a typical screen display obtained using the prior art apparatus to observe the left ventricular volume changes.
Figure 3B:
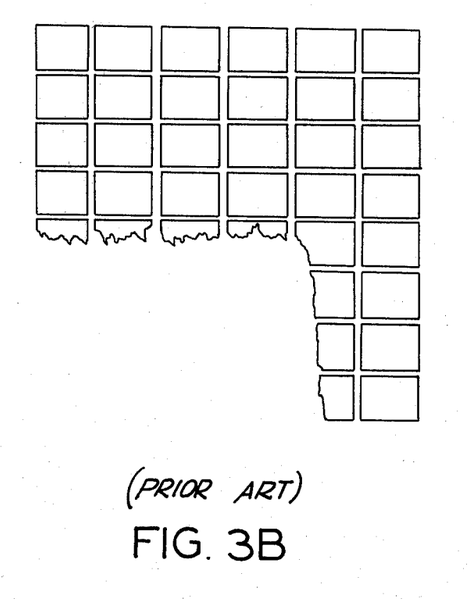
FIG. 3B is a typical screen display obtained using the prior art apparatus to measure tissue background activity.

The prior art apparatus is described in detail in Belgian Pat. No. 848072. Utilizing this apparatus in the manner described, data in the form of photographs may be obtained as shown in FIGS. 3A and 3B. FIG. 3A depicts a bar graph corresponding to changing left ventricular volume versus one average cardiac cycle. FIG. 3B depicts a bar graph corresponding to tissue background.

An estimate of left ventricular ejection fraction, a parameter commonly used in characterizing blood flow through the heart, may be obtained by manually measuring the photographic data. The equation defining ejection fraction (EF) is as follows:

$$\text{Ejection Fraction } EF = \frac{\text{End Diastolic Volume} - \text{End Systolic Volume}}{\text{End Diastolic Volume} - \text{Background}}$$

End Diastolic Volume approximately corresponds to the average bar length of the left peak of FIG. 3A. End Systolic Volume approximately corresponds to the average bar length of the valley of the bar graph of FIG. 3A. Background corresponds to the average bar length of FIG. 3B. Bars are measured from the bottom of the photograph. It is evident that these measurements are not easily made. The values obtained are entered into the above equation and the resulting ejection fraction recorded.

Figure 1:
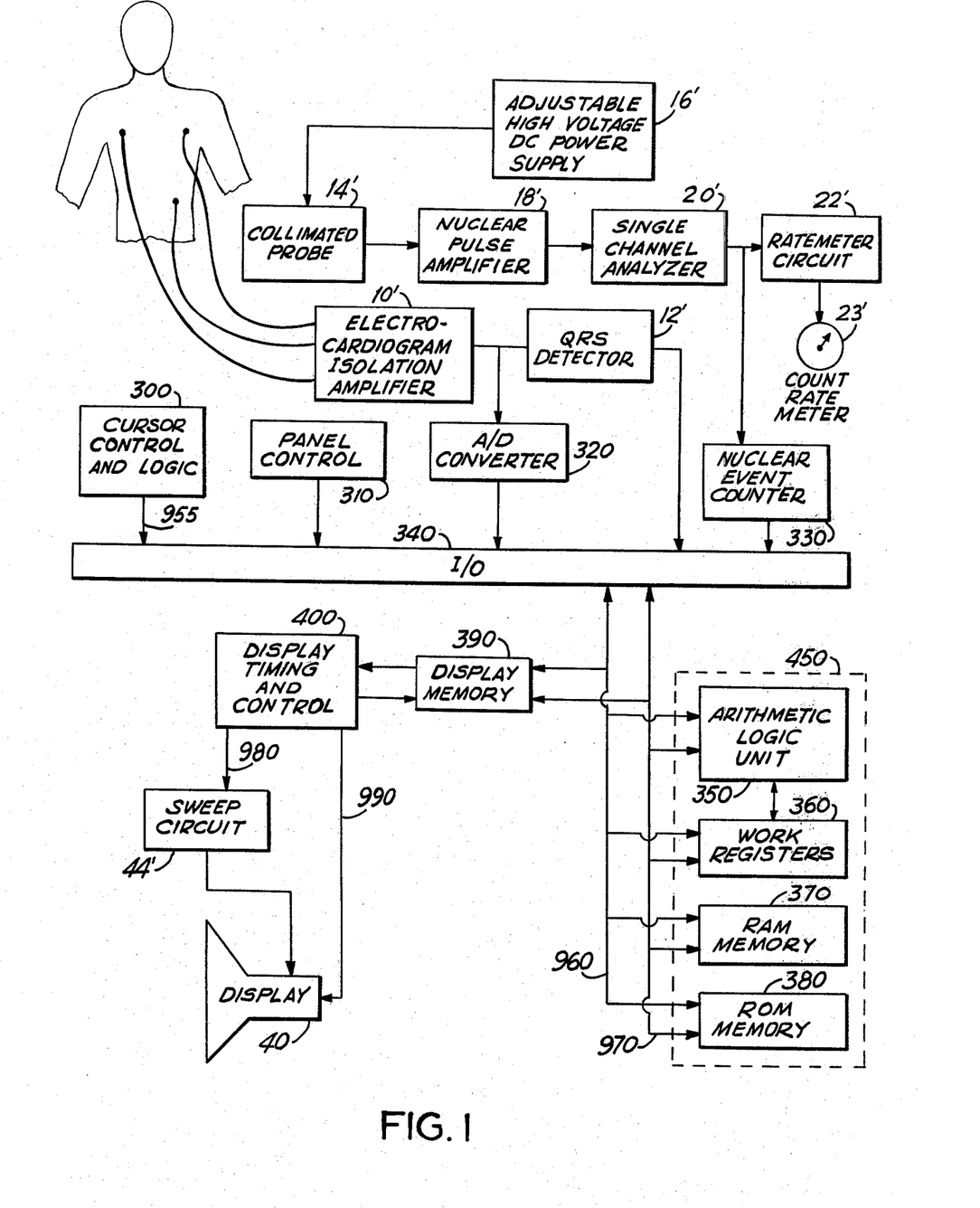
FIG. 1 is a block diagram of the preferred embodiment of the apparatus for characterizing blood flow through the heart, in accordance with the present invention.
Figure 1A:
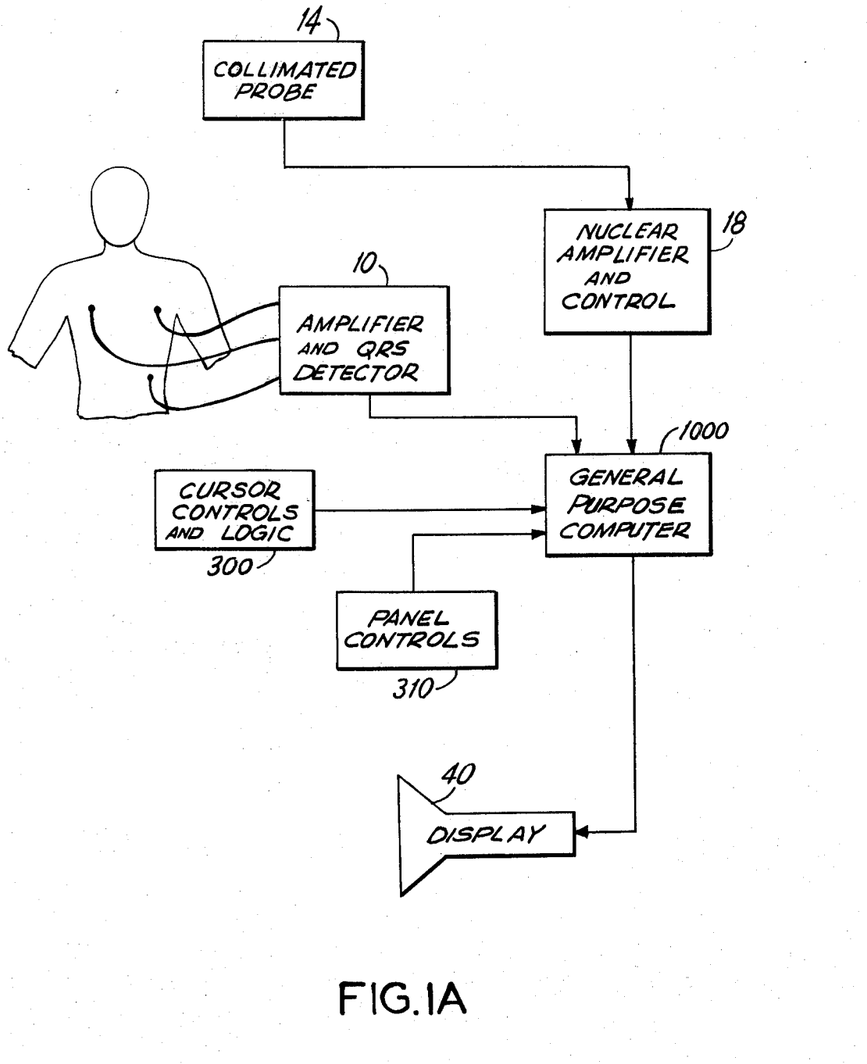
FIG. 1A is a simplified block diagram of the preferred embodiment of the apparatus for characterizing blood flow through the heart, in accordance with the present invention.

FIG. 1A illustrates a simplified block diagram of the apparatus of the present invention. Collimated probe 14, nuclear amplifier and counter 18, amplifier and QRS detector 10 and display 40 are as previously described with reference to FIG. 2. The output of nuclear amplifier and counter 18 passes to general purpose computer 1000 which, in part, stores counts in specific memory locations in synchronism with or independently of the output of amplifier and QRS detector 10 depending on the settings of panel controls 310. General purpose computer 1000 in conjunction with cursor controls and logic circuit 300 also causes cursors, which may be manually positioned, to be displayed with other data on display 40. Computer 1000 also calculates and displays certain parameters of interest as a function of cursor position in combination with data transmitted via nuclear amplifier and counter 18 and via amplifier and QRS detector 10.

Using the apparatus of FIG. 1A, illustrated in more detail in FIG. 1, in conjunction with the method disclosed herein, the displays depicted in FIGS. 4, 5, 6 and 7 may be generated which characterize blood flow through the heart on the basis of an average cardiac cycle. An alternate embodiment of the invention results in FIG. 8 in which blood flow through the heart is characterized on the basis of individual cardiac cycles. In still another embodiment, the display of FIG. 10 may be generated in which blood flow though the heat is characterized on the basis of transit time.

Figure 9:
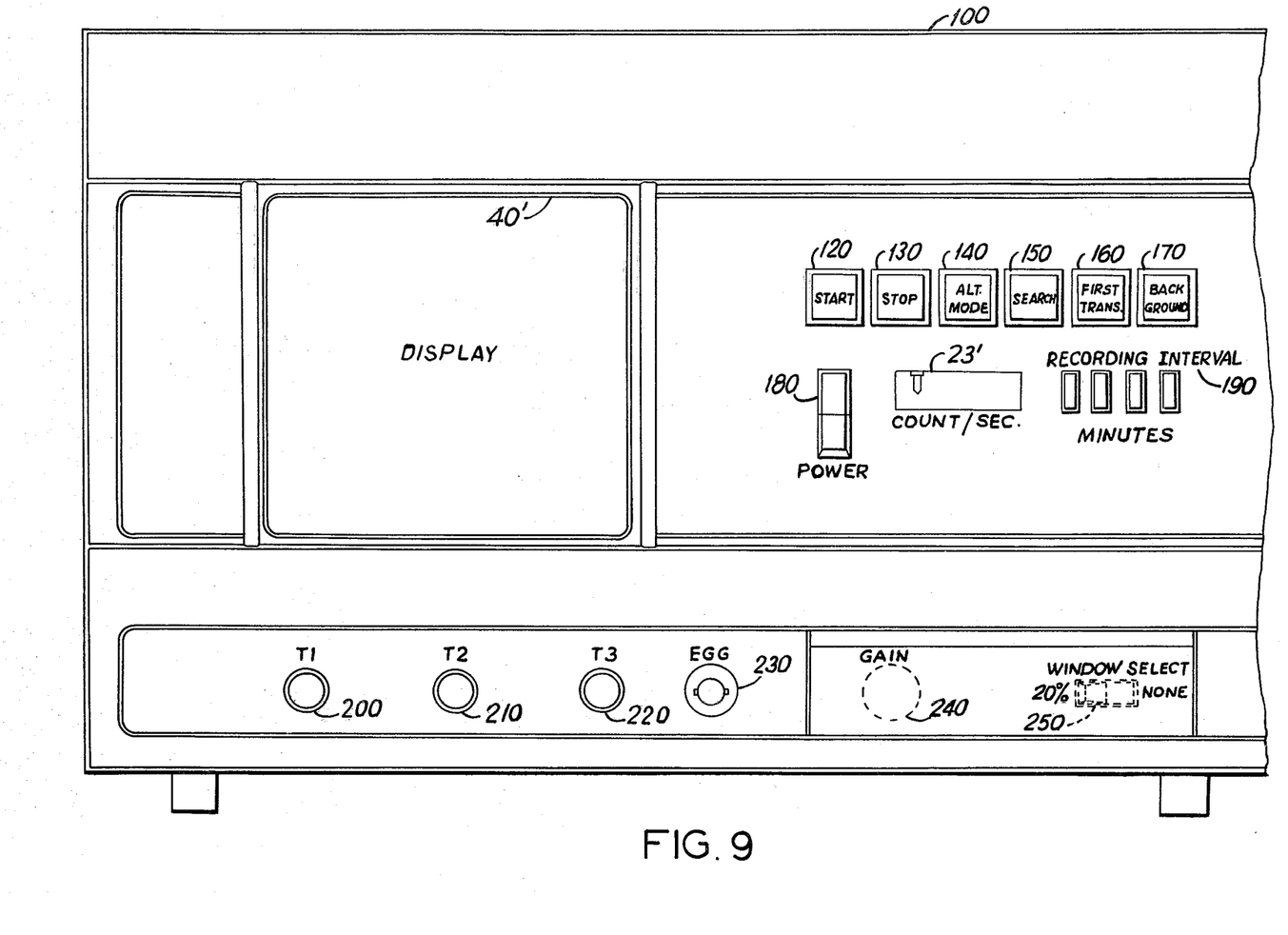
FIG. 9 shows a control panel configuration.

Referring to FIG. 1 taken in conjunction with FIG. 9 an improved apparatus is indicated having a collimated probe 14' powered by an adjustable supply (typically 800–1200 VDC) which is set by gain control 240. Collimated probe 14' preferably consists of a thallium-doped sodium iodide (NaI(Tl)) crystal 2 inches in diameter and ½ inch to 1 inch thick coupled to a photomultiplier detector. The crystal views nuclear radiation though a collimator preferably having a tapered internal opening converging toward the radiation source.

The output of collimated probe 14' is connected to nuclear pulse amplifier 18'. The output of nuclear pulse amplifier 18' is connected to single channel analyzer 20'. Single channel analyzer 20' circuitry is selectable by window select switch 250 and compares incoming data pulses to only a lower voltage threshold or both an upper and lower voltage threshold. The output of single channel analyzer 20' connects a ratemeter circuit 22' which drives count ratemeter 23' and also connects to nuclear event counter 330. The output of nuclear event counter 330 is connected to general purpose computer 450 via conventional input-output arrangement 340 which may consist, for example, of several Intel Corporation programmable peripheral inferface 8255 units.

Computer 450 is more particularly described as having an arithmetic logic unit (ALU) 350 in combination with work registers 360 to constitute a central processing unit (CPU) which may consist, for example, of an Intel Corporation silicon gate MOS microprocessor 8080A. A read only memory (ROM) 380, which may consist, for example, of an Intel Corporation silicon gate MOS reprogrammable read only memory 1702A, is programmed with the necessary control and computation algorithms. A random access memory (RAM) 370, which may consist, for example, of an Intel Corporation silicon gate MOS random access memory 2102A, is also provided to provide temporary storage of data and of values calculated in ALU 350.

The input of electrocardiogram isolation amplifier 10' is connected to the patient in the convention manner via panel connector 230 and the amplifier output is connected to conventional QRS detector 12' and conventional analog to digital (A/D) converter 320. A/D converter 320 may consist, for example, of an Analog Devices model 7570. The utputs of QRS detector 12' and A/D converter 320 connect to computer 450 via conventional I/O arrangement 340 which may consist, for example, of an Intel Corporation programmable peripheral interface 8255.

Panel controls 310, mounted on panel 100, preferably include Start Switch 120, Stop Switch 130, Alternate Mode Switch 140, Search Switch 150, First Transit Switch 160, Background Switch 170, Recording Interval Switches 190 and connect to Computer 450 via I/O Arrangement 340.

Cursor controls and logic 300 are implemented using standard hardware and software techniques known to one skilled in the art. Cursors T1, T2 and T3 are operated via controls 200, 210 and 220, respectively. Cursor controls and logic 300 connects to computer 450 via I/O arrangement 340.

Figure 1B:
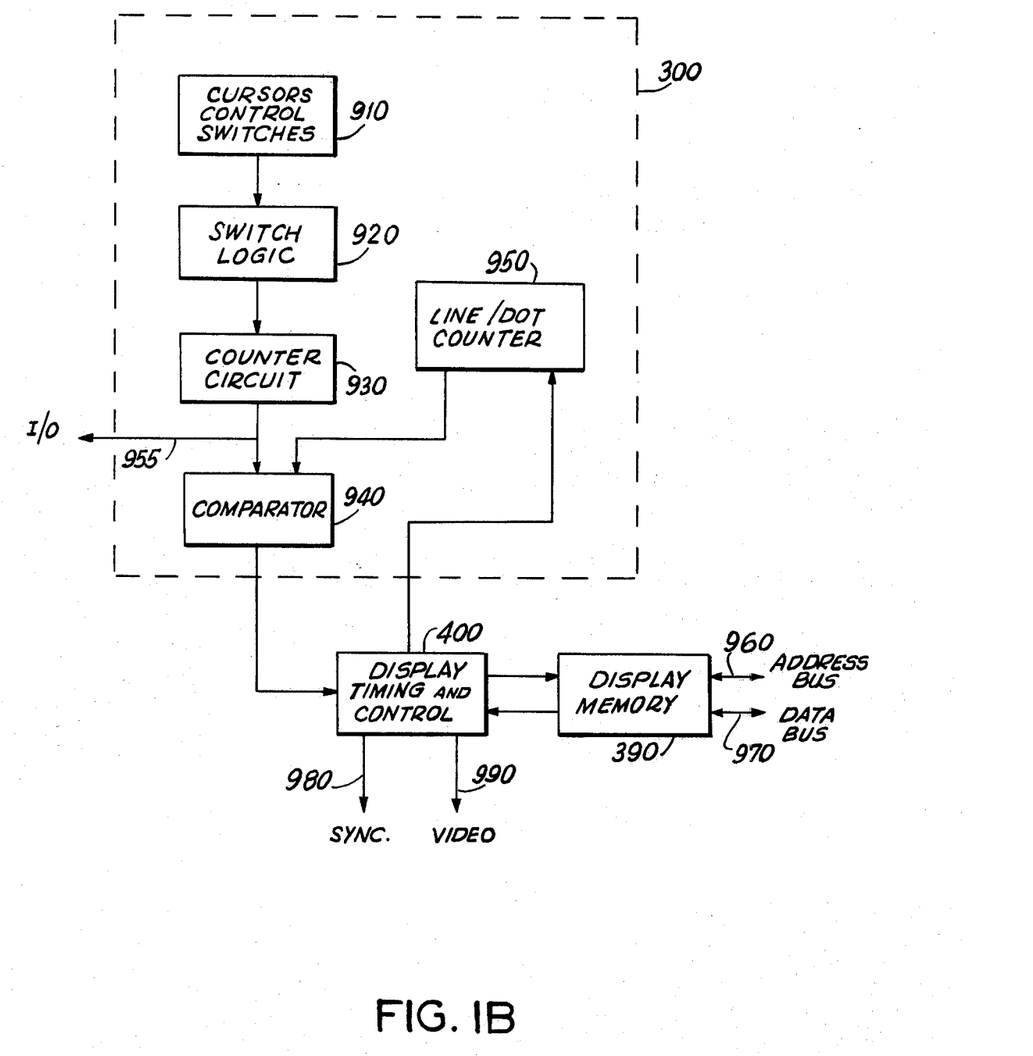
FIG. 1B is a block diagram of the cursor control and logic circuit.

Referring to FIG. 1B, a more detailed block diagram of the preferred embodiment of cursor controls and logic 300 is illustrated. Cursor control switches 910 consists of at least controls 200, 210 and 220 as shown in FIG. 9, and which connects to conventional debounce circuitry and logic gating in switch logic circuit 920. Switch logic 920 communicates with counter circuit 930 and clocks a counter associated with one of the cursor control switches up or down depending on the desired cursor motion. The counter output communicates with I/O arrangement 340 via signal 955. In FIG. 1B and others, a signal line such as 955 may represent a plurality of parallel signals not shown for reasons of clarity. Signal 955 also communicates with comparator 940 which compares signal 955 to the output of line/dot counter 950 which is clocked by signals from display timing and control 400 representing display lines or dots. Each time the inputs of comparator 940 are in coincidence, the output signal passing to display timing and conrol circuit 400 causes a portion of a suitable cursor to be generated on display 40'.

Display timing and control circuit 400 provides appropriate synchronization pulses via signal 980 to TV sweep circuits 44' which drive deflection coils of convention raster display unit 40'. Display timing and control circuit 400 provides suitable video signals to display 40' via signal 990 and is also connected to display memory 390 which may consist, for example, of a random access memory AM9130ADC manufactured by American Micro Devices. Display memory 390 connects to address bus 960 and data bus 970 via which it communicates with computer 450. Display timing and control circuit 400 utilizes techniques known in the art for generating dot patterns and alphanumeric characters on a raster type display.

Displaying timing and control circuit 400 consists of conventional TTL and Schottky TTL logic in combination with a character generator, e.g. Signetics 2513, arranged so as to read the contents of display memory 390 with suitable clocking signals and communicate the contents of display memory 390 to display 40' and sweep circuits 44' by generating SYNC signals 980 and video signal 990 in a conventional manner. Sweep circuits 44' and display 40' may be, for example, obtained as a Ball Brothers CRT Model TV-9W.

With the patient previously injected with a suitable radioactive blood pool tracer, e.g. Technetium-99m tagged human serum albumin, and with the apparatus connected to the patient and with collimated probe 14' set in proximity to the body as described above, a measurement of left ventricular heart function may now be made. Operating Power Switch 180 causes circuts in the apparatus to be energized. With collimated probe 14' in a suitable position for measuring tissue background radioactivity, Background Switch 170 may be operated causing computer 450 to accumulate pulses corresponding to the nuclear events observed by collimated probe 14'. The gamma radiation caused by nuclear disintegration events in tissue is collected through the collimator of collimated probe 14' and causes the NaI (Tl) crystal to fluoresce. The fluorescence is observed by the photomultiplier which in turn causes current pulses to be generated at its output. The output current pulses are amplified and converted into voltage pulses by nuclear pulse amplifier 18', which are passed to a single channel analyzer 20'. Single channel analyzer 20' compares these voltage pulses to pre-established low voltage threshold and high voltage threshold levels. Voltage pulses exceeding the low voltage threshold but not the high voltage threshold are classified as representing valid gamma radiation and cause a digital pulse output from single channel analyzer 20'. These digital pulses are counted by nuclear event counter 330 and also converted into a suitable output to drive count ratemeter 23' by ratemeter circuit 22'.

Operation of Background Switch 170 also causes computer 450 to transfer counts from nuclear event counter 330 and accumulate them in RAM 370 according to an algorithm programmed in ROM 380. The algorithms indicated herein are based on the instruction set of the microprocessor used as computer 450 and may readily be derived by one skilled in the art of microprocessor programming. The algorithm may cause counts to be accumulated up to a preset limit, e.g. 50,000 counts, or for a preset time, e.g. 30 seconds. At the end of this period, computer 450 may cause a message to the operator to be displayed on Display 40' via address bus 960, data bus 970, display memory 390 and display timing and control circuit 400 indicating the completion of background measurement. The background rate in counts per second may also be displayed.

With collimated probe now in position over the left ventricle, a recording interval of, for example, 1, 2, 4 or 8 minutes may be selected using switches 190. Operating Start Switch 120 now causes computer 450 to collect data in synchronism with the electrocardiogram signal of the heart. The electrocardiogram signal is amplified and extraneous muscle noise is filtered by electrocardiogram isolation amplifier 10'. The output of amplifier 10' passes to A/D converter 320 which produces a suitable digital signal and also passes to QRS detector 12' which produces a synchronization pulse when the R-S portion of the electrocardiogram is detected.

At the occurrence of the synchronization pulse, computer 450, in accordance with an algorithm programmed in ROM 380, transfers counts from nuclear event counter 330 to RAM 370 using a unique memory location for each of a plurality of short counting intervals. The horizontal time axis of the cathode ray tube display corresponds to the previously determined number of counting intervals. The counting interval may be, for example, 10 milliseconds, and the number of these subintervals is conveniently chosen as 256. The next synchronization pulse from QRS detector 12' may occur prior to or after 256 intervals have passed, depending on heart rate. At the next synchronization pulse, counts from nuclear event counter 330 for a given counting interval are added to counts previously stored in RAM 370 for a corresponding counting interval. The accumulation of counts continues until the end of the selected recording interval.

Figure 4:
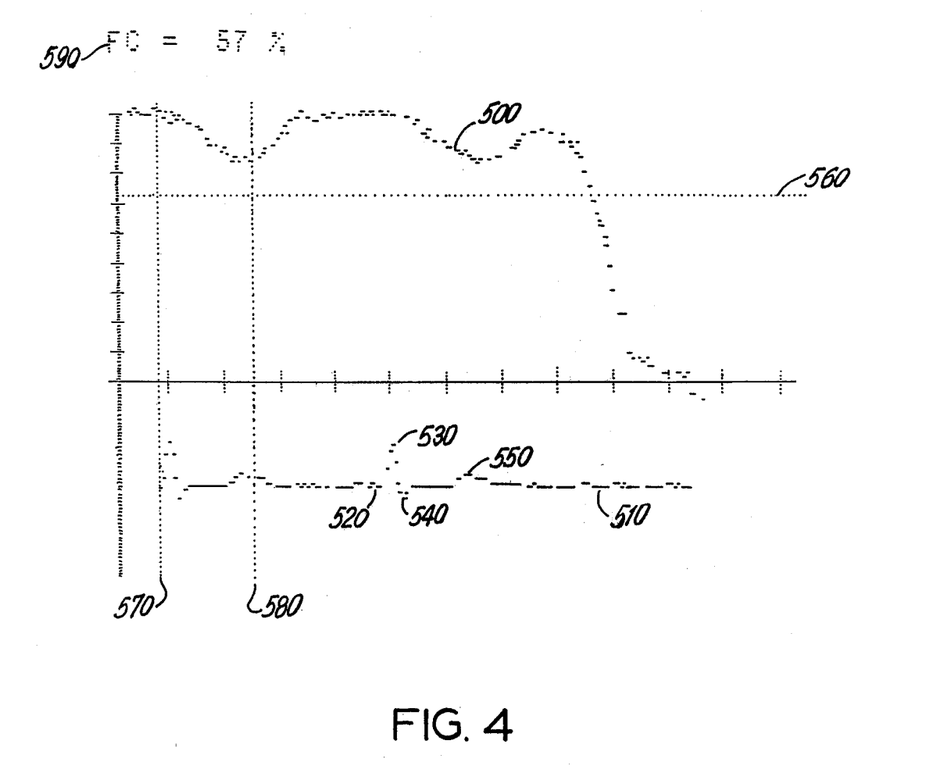
FIG. 4 is a typical screen display obtained utilizing the preferred embodiment of the apparatus for characterizing blood flow through the heart, in accordance with the present invention, to observe the left ventricular volume changes.

During and after the selected recording interval, computer 450, in accordance with an algorithm programmed in ROM 380, communicates to display memory 390 via address bus 960 and data bus 970 a desired dot pattern which when shown on display 40' via diaplay timing and control circuit 400 is similar to FIG. 4. After the recording interval is completed, the contents of display memory 390 continue to be displayed on Display 40'.

Referring to FIG. 4, curve 500 depicts left ventricular volume varying two cardiac cycles. By accumulating data over two cardiac cycles, rather than one cardiac cycle, the possibility of losing relevent information due to the non-uniformity of the cardiac cycle is minimized. The curve is composed of dots representing the counts accumulated in each 10 millisecond counting interval. These dots are equivalent to the tops of the bars depicted in FIG. 3A using the prior art apparatus. Curve 510 is an approximation of the electrocardiogram of the patent. Data for curve 510 is obtained through A/D convertor 320 via I/O arrangement 340 to computer 450. Areas 520, 530, 540 and 550 of curve 510 represent portions of the electrocardiogram conventionally known at the Q-wave, R-wave, S-wave and T-wave, respectively. Since two average cardiac cycles are displayed, the Q, R, S and T-waves are shown twice. Horizontal line 560 represents the level of tissue background activity previously measured and which is scaled to be in proportion to curve 500 by an algorithm programmed in ROM 380. Vertical lines 570 and 580 represent cursors which may be moved horizontally across the display in either direction via the operation of, for example, controls 210 and 220, respectively. Alphanumeric expression 590 represents the fractional change between the intersection of cursor 580 with curve 500 and the intersection of cursor 570 with curve 500, expressed as a percentage of the distance between the intersection of cursor 570 with curve 500 and the intersection of cursor 570 with line 560. This expression is calculated by computer 450 in accordance with an algorithm programmed in ROM 380. Data to display curve 500 has previously been stored in RAM 370. The positions of cursors 570 and 580 relative to the 256 intervals are communicated to computer 450 from cursor controls and logic circuit 300 via I/O arrangement 340 and signal 955.

In the method of obtaining an estimate of ejection fraction of the left ventricle, cursor 570 is moved horizontally using control 210 until cursor 570 intersects the left most Q-wave of curve 510. Cursor 580 is moved horizontally using control 220 until cursor 580 approximately bisects T-wave 550. These are conventionally suitable points for determining ejection fraction, but medical judgement may indicate other suitable positioning for various pathological conditions. The intersections of cursors 570 and 580 with curve 500 are now at end diastolic volume (EDV) and end systolic volume (ESV) respectively. Computer 450 immediately computes and displays fractional change 590 (FC) corresponding to ejection fraction (EF) according to the algorithm:

$$FC = EF = \frac{EDV - ESV}{EDV - \text{Background}}$$

In order to improve the statistical accuracy of the computation of expression 590, and algorithm may be devised so as to average the counts of intervals adjacent to the intersections of, for example, cursors 570 and 580 with curve 500, the number of intervals conveniently chosen as 5.

Figure 5:
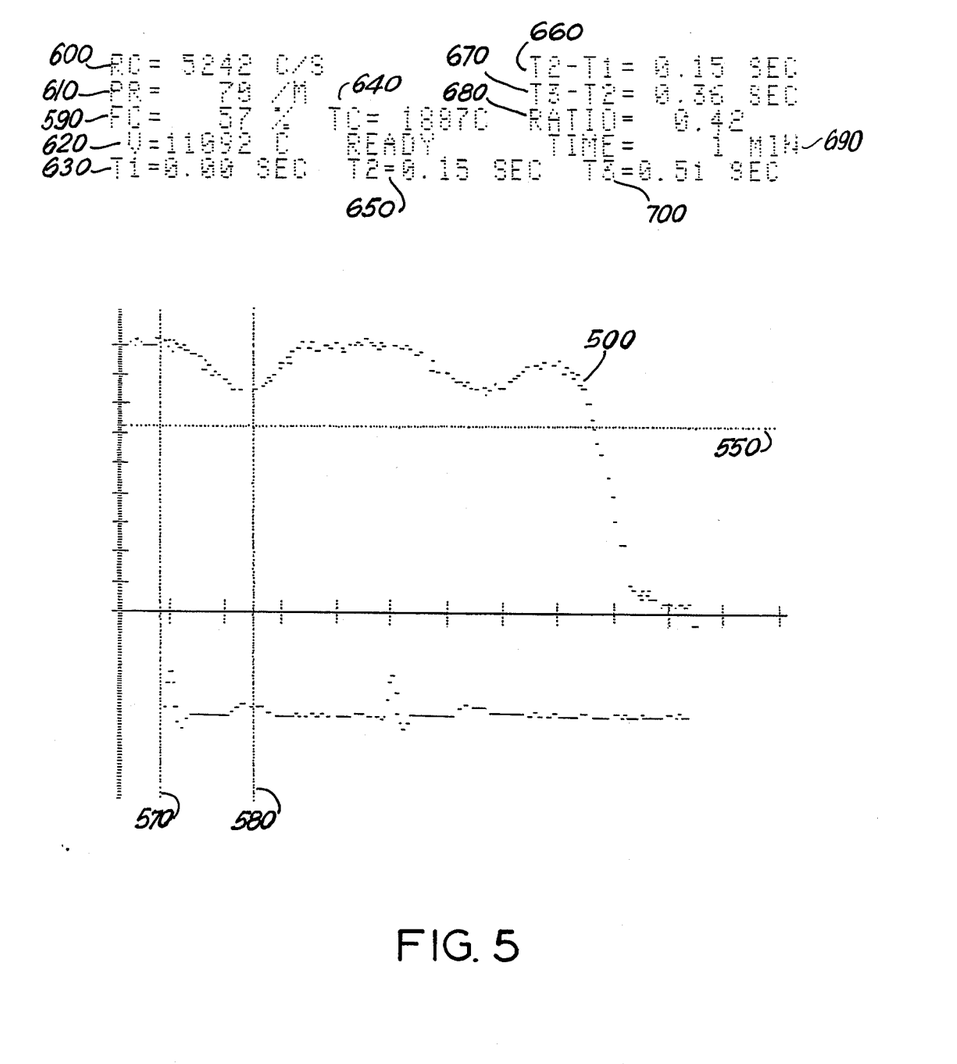
FIG. 5 is a typical screen display containing additional computed information.
Figure 6:
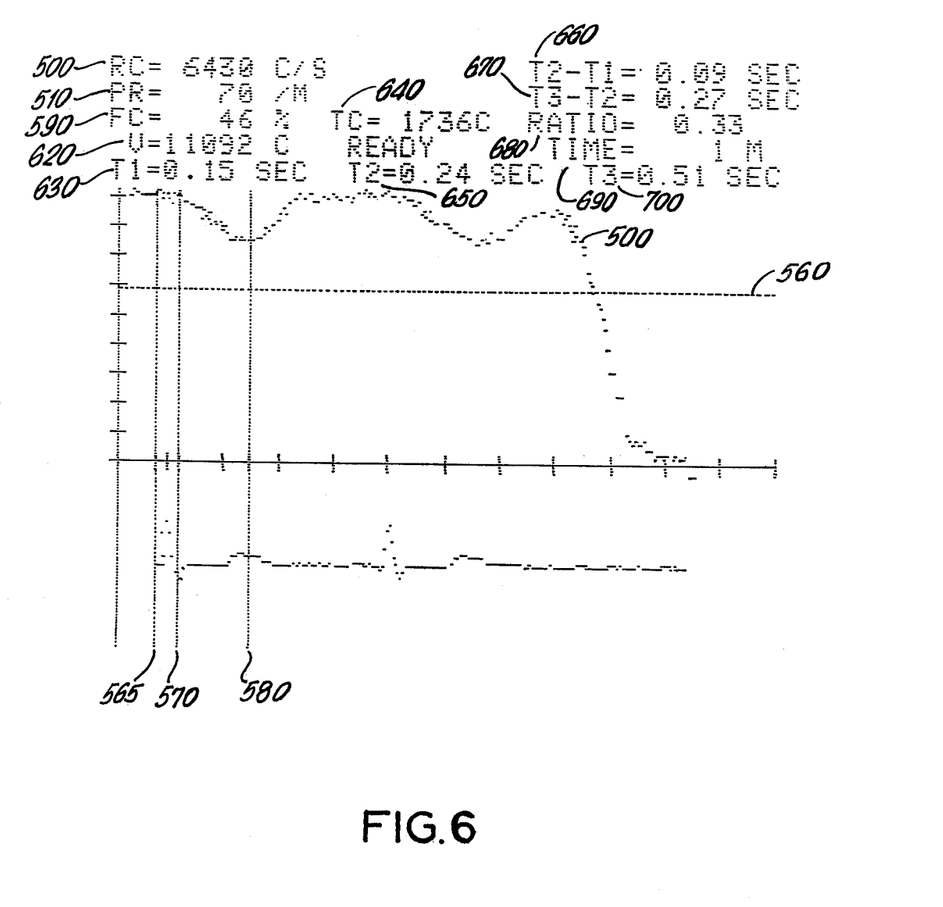
FIG. 6 is the display of FIG. 5 with an additional cursor.

An alternate embodiment of the present invention is shown in FIG. 5 wherein other alphanumeric expressions suitable for further characterizing blood flow through the heart are calculated and displayed by computer 450. Another alternate embodiment is shown in FIG. 6 wherein a third cursor 565 operated by control 200 is shown. Referring now to FIGS. 5 and 6 the following expressions may, for example, be displayed:

Expression 600, Rate of Change (RC) of curve 500

$$RC = \frac{\text{Counts at 570 intersection minus counts at 580 intersection}}{\text{Time between 570 and 580}},$$

expressed in counts per second.

Expression 610, pulse rate (PR) equal to the number of patient R-waves per minute.

Expression 620, vertical scale (V) equal to the maximum counts per 10 millisecond interval of curve 500, expressed in counts.

Expression 640, Total Change, (TC) of curve 500. TC=Counts at 570 intersection—counts at 580 intersection, expressed in counts.

Expression 630, time setting $T_1$ of cursor 565, referenced to vertical axis, expressed in seconds.

Expression 650, time setting $T_2$ of cursor 570, referenced to vertical axis, in seconds.

Expression 700, time setting $T_3$ of cursor 580, referenced to vertical axis, in seconds.

Expression 660, time difference $T_2-T_1$ between cursors 570 and 565, in seconds.

Expression 670, time difference $T_3-T_2$ between cursors 580 and 570, in seconds.

Expression 680, ratio of expression 660 to expression 670.

Expression 690, recording interval selected using switches 190.

The above expressions may be used singly or in combination to obtain rates of change of selected portions of curve 500 or to obtain the times of occurrence of selected features of curve 500 relative to the length of the cardiac cycle.

Figure 7:
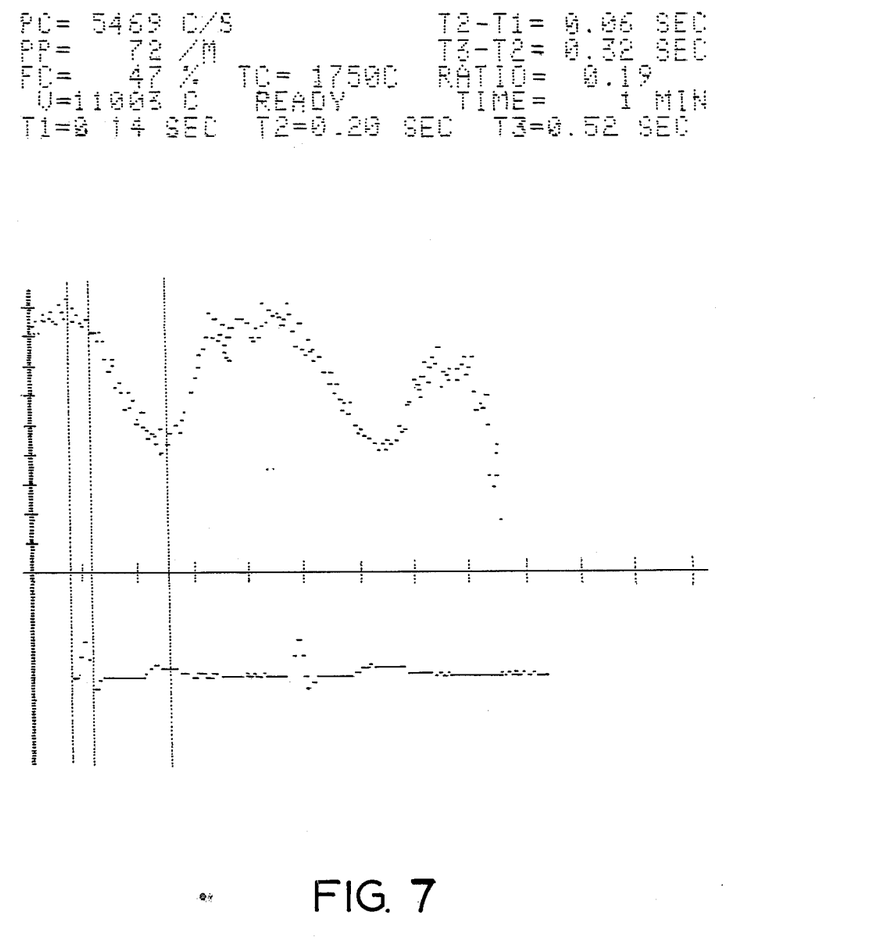
FIG. 7 is the display of FIG. 5 with an expanded vertical scale applied to the curve of left ventricular volume.

An alternate embodiment of the present invention is shown in FIG. 7, wherein curve 500 is expanded vertically by shifting line 560 downwards to coincide with the horizontal axis and proportionally shifting the points of curve 500, previously above line 560, downward. This permits features of curve 500 to be more clearly identified. FIG. 7 may be generated by operating alternate mode switch 140 which communicates with computer 450 via I/O arrangement 340 causing the display dot pattern to change according to an algorithm programmed in ROM 580.

Figure 8:
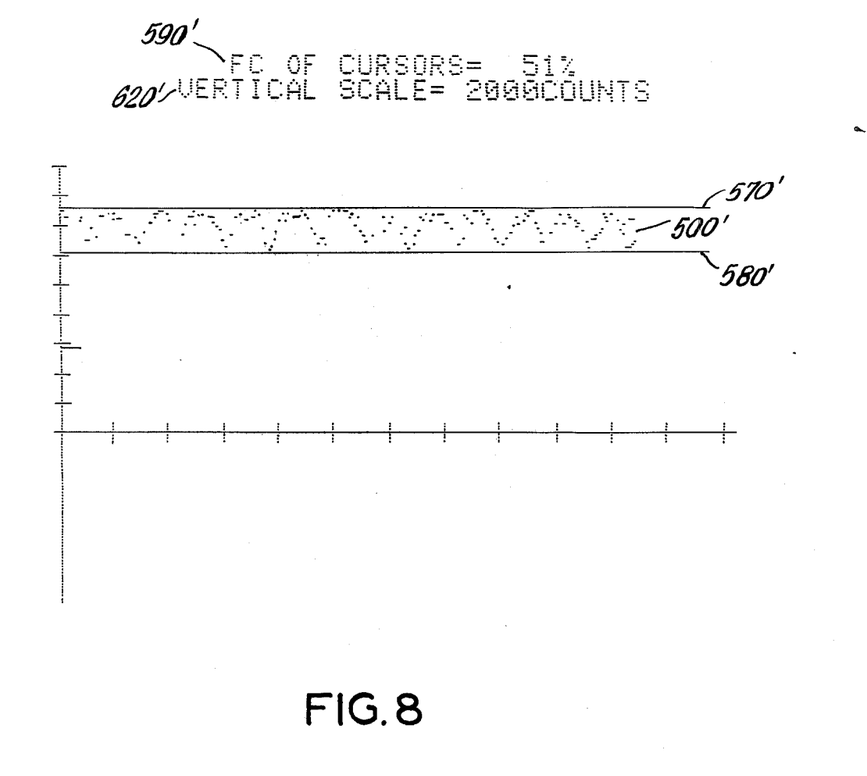
FIG. 8 illustrates an alternate method of utilizing cursors to characterize blood flow through the heart.

An alternate embodiment of the present invention is shown in FIG. 8 wherein blood flow through the heart may be characterized for the individual heart beats as opposed to accumulating counts to construct an average cardiac cycle. In certain pathologies of the heart, blood flow may vary from beat to beat and the present invention permits the estimation of left ventricular ejection fractions for selected heartbeats via the use of horizontal cursors.

Referring now to FIG. 8, in the method for estimating left ventricular ejection fractions of individual heart beats, operating search switch 150 causes via a connection (not shown) cursor controls and logic circuit 300 to communicate to computer 450 the positions of cursors 570' and 580' relative to the vertical scale of FIG. 8. Further, operating search switch 150 causes computer 450 to transfer counts from nuclear event counter 330 to RAM 370 as previously described using longer counting intervals, for example 50 milliseconds, with the total number of subintervals remaining at 256. In this manner, curve 500' is displayed showing a plurality of individual cardiac cycles as they occur, the number of cycles depending on the patient's heart rate. Curve 500' is traced across the display without need of synchronization with the electrocardiogram. This embodiment, therefore, permits the use of the apparatus and method for exercise studies of patients, where additional muscle noise may make synchronization difficult. Curve 500' is traced across the display until the last counting interval is completed. Thereafter, the tracing of curve 500' is erased and a new tracing begins at or near the vertical axis. The retracing of curve 500' can continue as long as desired. Operation of Stop Switch 130 causes tracing of curve 500' to stop, without erasing the display.

During the tracing of curve 500' or after stopping, cursors 570' and 580' may be adjusted using controls 210 and 220 respectively so as to intersect the peak and valley of selected cardiac cycles or to intersect several simultaneously. Computer 450 immediately calculates expression 590' according to the algorithm previously described, which provides an estimate of the ejection fraction.

The method of FIG. 8 may also be used to assist in the positioning of collimated probe 14' wherein the user observes changes in the position and amplitude of curve 500' while manipulating collimated probe 14' in proximity to the left ventricle. In this embodiment of the invention, Computer 450 may be used to calculate and display parameters, on a beat-by-beat basis or utilizing a combination of data obtained with several heart beats, which assist the user in locating the optimum position for measuring left ventricular activity or measuring tissue background activity. For example, empirical data has shown that a suitable position for measuring tissue background activity exists where the measured count rate is low and exhibits no synchronism with the heart rate. Therefore, an algorithm devised to compute and display the degree of synchronism of data with the heart rate as a function of each heart beat would guide the user in optimally positioning the collimated probe. This may be done in numeric form or as a graphic representation. Similarly, an algorithm may be devised which computes and displays to the user a numeric or graphic representation which guides the user in optimally positioning collimated probe 14' in proximity to the left ventricle. Curve 500 may be automatically proportioned to the vertical axis and vertical scale 620' computed and displayed by computer 450. Alternatively, vertical scales may be manually selectable from control panel 100 via switches (not shown).

In another embodiment, Computer 450 may be used to measure and store in RAM 370 successive heart beat intervals concurrently with or independently of nuclear event data. Computer 450 may then be caused to compute and display a numeric or graphic representation of the statistical distribution of measured intervals about some mean value.

Referring to FIGS. 4, 5, 6, 7 and 8, it is often convenient for the user of the apparatus to measure and store tissue background radioactivity after performing left ventricular measurements. ROM 380 may be programmed to respond to a sequence of operations of control panel switches so as to permit the measurement and storage of tissue background without the loss of left ventricular data and to include new background data in the displayed curves and expressions.

Figure 10:
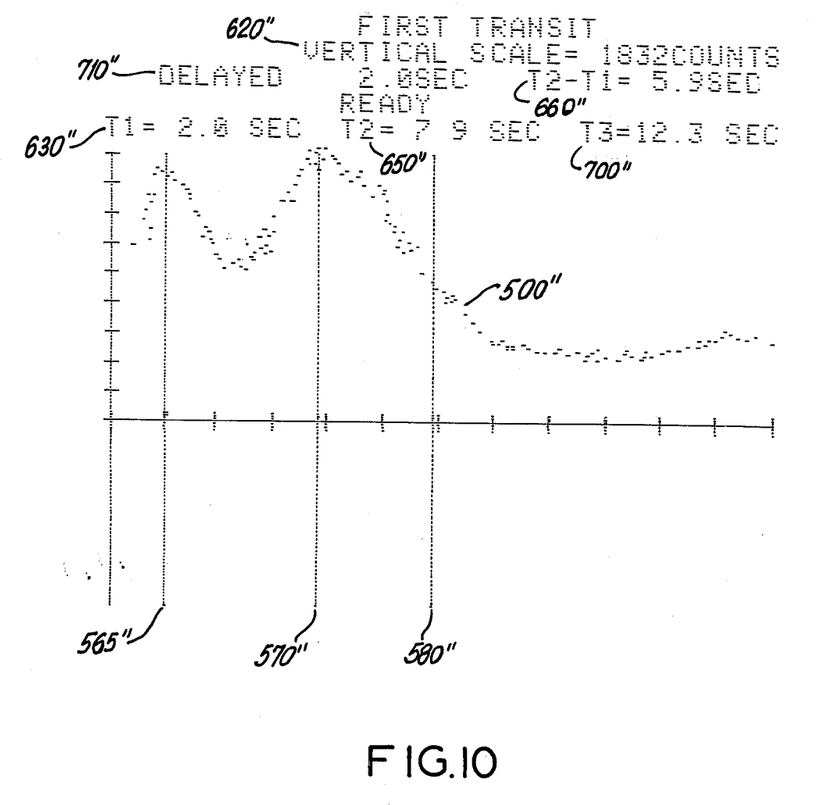
FIG. 10 illustrates an alternate embodiment for measuring cardiac transit time.

An alternate embodiment of the invention is illustrated in FIG. 10 wherein the injected bolus of radioactive solution is measured and displayed as it passes through the chambers of the heart and the time of passage between the right ventricle and left ventricle, conventionally known as transit time, is measured using cursors 565" and 570". In the method of measurement, the orientation and position of the heart is determined by the physician by conventional auscultation and palpitation. Collimated probe 14' is then positioned so as to have both right and left ventricles in the collimator field of view. At the moment of injection of the radioactive bolus into the patient, first transit switch 160 is operated, causing computer 450 to compare counts in nuclear event counter 330 against a predetermined level, for example 4000 counts. When this level is reached, indicating that the injected bolus is nearing the heart, computer 450 begins to transfer without displaying, counts from nuclear event counter 330 to RAM 370 as previously described except that counting intervals are, for example, 100 milliseconds with the total remaining at 256. After enough time has elapsed as so to allow passage of the bolus through both ventricles, for example 12 seconds, curve 500" is automatically proportioned to the vertical axis and displayed. Computer 450 continues to accumulate count data until 256 counting intervals have occurred and then stops. Cursor 565" is then centered on the first peak of curve 500" and cursor 570" on the second peak of curve 500" using controls 200 and 210 respectively. Expression 660" is immediately calculated and displayed by computer 450 as previously described, and is an estimate of the transit time of the heart. Other expressions which may be displayed are cursor time expressions 630", 650", 700", vertical scale 620" and delay time 710" which corresponds to the interval between the operation of first transit switch 160 and the time that a threshold of counts is exceeded by nuclear event counter 330. Cursor 580" need not be used.

Other embodiments of the apparatus and method are possible including the use of a conventional nuclear medicine scintillation camera in place of collimated probe 14'. Further, the apparatus and method of the present invention may be used to characterize blood flow through major arteries or other organs such as the brain or kidneys. A further embodiment may include the use of conventional digital thumbwheel switches on the control panel with which to enter, for example, the concentration in the blood of the radioactive isotope so as to calculate and display actual blood volumes using computer 450. in still another embodiment, irregular heartbeat intervals can be monitored and, for example, the percent of heartbeat intervals shorter than the average interval and the percent longer than the average can be calculated and displayed. Further, displayed figures may be reproduced on any copying device having video input capability by connecting the signals applied to Display 40' to such a device, for example, a Tektronix 4632.

What is claimed is:

1. Apparatus for characterizing blood flow through a heart for analysis of individual cardiac cycles comprising:
   a nuclear detector probe responsive to the radioactive output of a radioactive trace introduced into a patient's blood stream to provide an output indicating the amount of radioactivity at a selected location of the heart blood pool,
   a time base generator to provide a time base that is divided into successive time intervals,
   a counter of said detector output,
   a memory to store counts from said counter over each of said time intervals,
   a programmable computer responding to said counts of certain of said time intervals to compute the value of a predetermined parameter of the patient's blood flow simultanous with each cardiac cycle being detected,
   a display of said value of said predetermined parameter substantially simultaneous with the computation thereof,
   said computer calculations and said display being substantially simultaneous with the production of said detector output signal and changing in response to changes of said detector output signal.

2. The apparatus of claim 1 further comprising: a display of said counts over each of said time intervals along said time base to provide a graphical display of each cardiac cycle simultaneous with said display of said value.

3. The apparatus of claim 2 wherein change of position of said nuclear detector causes change of said value of said predetermined parameter.

4. The apparatus of claim 1 wherein change of position of said nuclear detector causes change of said value of said predetermined parameter.

5. The apparatus of claim 4 wherein said predetermined parameter is left ventricle ejection fraction.

6. Apparatus for characterizing blood flow through a heart comprising:
   a nuclear detector probe responsive to the radioactive output of a radioactive trace introduced into a patient's blood stream to provide an output indicating the amount of radioactivity at a selected location of the heart blood pool,
   a receiver of a cardiogram signal to provide a synchronizing signal,
   a time base generator responsive to said synchronizing signal to provide a time base that is a function of the cardiac cycle, said time base being divided into successive time intervals,
   a counter of said detector output,
   a memory to store counts from said counter over each of said time intervals and to accumulate counts from corresponding time intervals of successive time base periods,
   a graphical display coupled to said memory store to provide a display of said detector output by said intervals along said time base, said display being based on said accumulated counts within corresponding time intervals over a predetermined number of time base periods and being continuously updated as each cardiac cycle is detected, and
   a programmable computer responsive to at least two selected values from said graphical display to calculate the value of a predetermined parameter of the patient's blood flow and to continuously update said calculation as each cycle is detected
   said computer calculations and said display of said value of said parameter being substantially simultaneous with the production of said detector output.

7. The apparatus of claim 6 further comprising: at least two manually movable cursors orthogonal to said time base to permit a user to select said two selected values of said display.

8. The apparatus of claim 6 wherein said time base is at least two cardiac cycles.

9. The apparatus of claim 8 wherein said predetermined parameter is left ventricle ejection fraction.

10. The apparatus of claim 6 wherein said predetermined parameter is left ventricle ejection fraction.

11. The method of characterizing blood flow through a heart for analysis of individual cardiac cycles wherein a nuclear detector probe is responsive to the radioactive output of a radioactive trace at a selected location of the patient's blood pool to provide an output that is counted by a counter and which is stored in a memory for each of successive predetermined time intervals over a time base that is divided into successive time intervals, the improvement comprising the steps of:

selecting the count value in certain of said time intervals, computing the value of a predetermined parameter of a patient's blood flow from said selected counts, said steps of selecting and computing being substantially simultaneous with each cardiac cycle that provides the output being detected by the detector, displaying said computed value of said predetermined parameter substantially simultaneous with the computation thereof, and updating said computed value of said predetermined parameter in response to changes of said detector output signals.

12. The method of claim 11 further comprising the steps of:

moving the detector to various locations over the chest of the patient, observing the changes of said computed value of said parameter to determine the region of interest as a function of optimized parameter value, and positioning and detector at said region of interest.

13. The method of claim 12 wherein said predetermined parameter is left ventricle ejection fraction.

14. The method of claim 11 further comprising the step of:

displaying said counts over each of said time intervals along said time base to provide a graphical display of the cardiac cycle substantially simultaneous with the cardiac cycle being detected and simultaneous with said computed value being displayed.

15. The method of claim 11 further comprising the steps of:

generating a synchronizing signal from the patient's cardiogram, synchronizing said time base with said synchronizing signal, storing the count value in each of said time intervals, accumulating counts in corresponding time intervals of successive time base periods, and graphically displaying the accumulated counts of said detector output by said intervals within said time base to provide a graphical display of the cardaic cycle simultaneous with said computed value being displayed.

16. The method of claim 15 further comprising the step of:

positioning manually movable cursors, orthogonal to said time base to select two values of said graphical display for the calculation of said predetermined parameter.

17. The method of claim 15 wherein said predetermined parameter is left ventricle ejection fraction.

18. The method of claim 11 wherein said predetermined parameter is left ventricle ejection fraction.

* * * * *